CHRYSANTHEMUM PLANT
Filed May 18, 1973
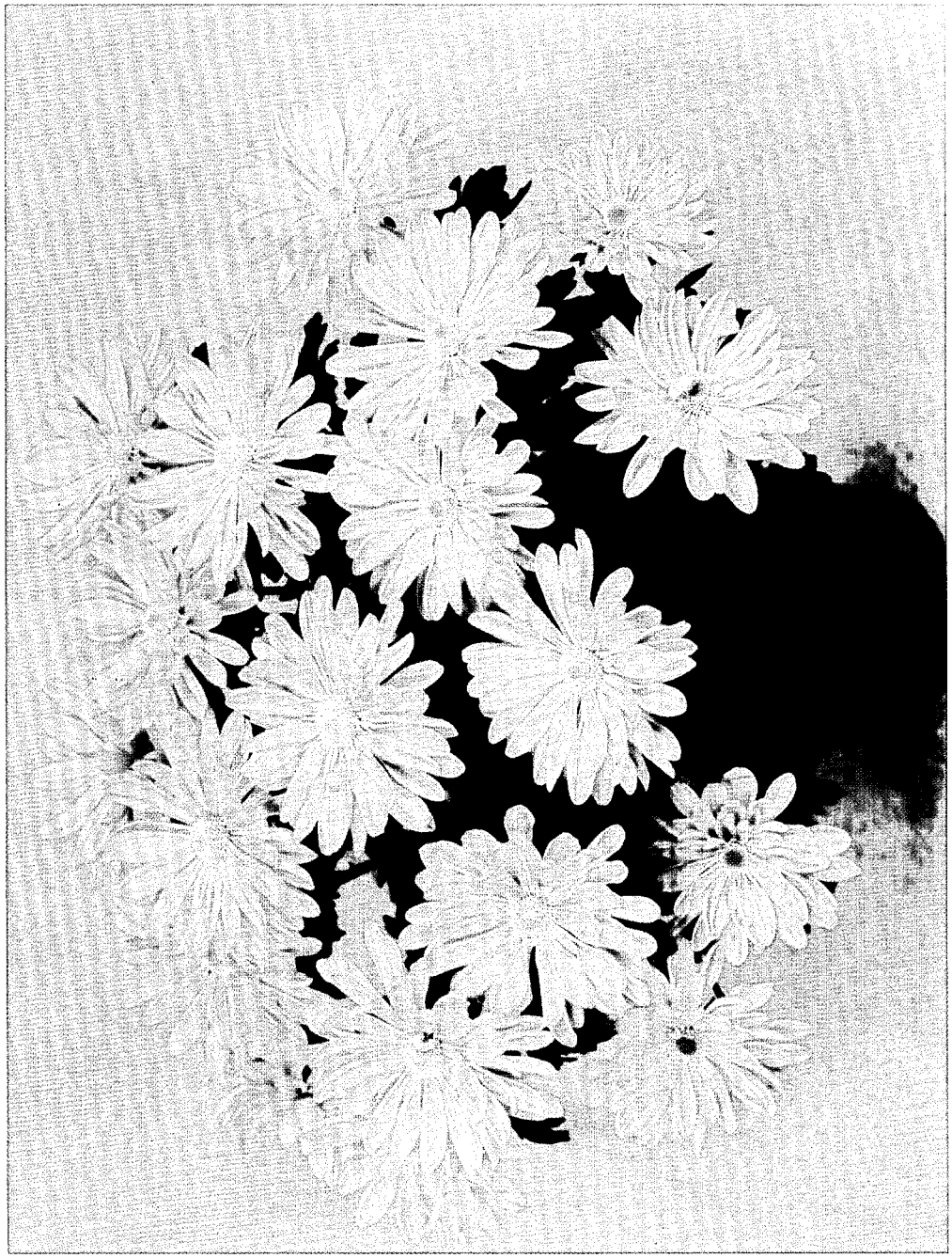

United States Patent Office

Plant Pat. 3,629

Patented Oct. 1, 1974

3,629
CHRYSANTHEMUM PLANT

Walter H. Jessel, Jr., Doylestown, and William E. Duffett, Akron, Ohio, assignors to Yoder Brothers, Inc., Barberton, Ohio

Filed May 18, 1973, Ser. No. 361,445
Int. Cl. A01h *5/00*
U.S. Cl. Plt.—74 1 Claim

The present invention comprises a new and distinct cultivar of chrysanthemum plant known by the varietal name Senorita which is a seedling of unknown parentage. The seedling was discovered as a growing and flowered plant in a cultivated area.

The new cultivar is similar in certain respects to the well known, unpatented cultivar Marguerita, having the following identical characteristics:

1. A large daisy-type flower (single) which is grown as a disbudded, single stem or pinched pot mum.
2. Requires tall treatment as a pinched disbudded pot plant.

The new cultivar is distinguished from Marguerita by the following characteristics, when grown under comparable conditions:

1. A pink flower color, with the cultivar Marguerita being ivory white.
2. A more fully petalled flower.
3. Petals approximately ½″ narrower, with numerous seta (commonly referred to as whiskers in the trade) on the ventral side of the petal.
4. Flowers approximately ¼″ smaller in diameter.
5. Less tolerance to temperatures lower than 60° F. for bud development. It will initiate and develop uniformly, but response is delayed. Marguerita has a faster, more uniform response when buds are developed at less than 60° F.
6. Approximately 2″ less vigor and approximately 2″ more spreading habit.

7. More responsive to the growth regulator Alar, thereby making it easier to control height.
8. A lighter green foliage.
9. Less indentations on the leaf margin.
10. Approximately 2 days earlier response (at 60° F.) for bud initiation and development, except in early spring when the response is 2 days later.

The new cultivar was selected from the progeny of an unknown cross and when asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from January through December; coastal California, January through December; southeastern and southwestern United States, January through December; and southern Florida, December through April.

The accompanying photographic drawing comprises a specimen photograph of the new cultivar grown in pot form, and shows the unique characteristics of the new cultivar, with the color being as nearly true as possible with color illustrations of this type. In the following description, color references are made in the Munsell Limit Color Cascade Chart, 1972 edition, in certain instances in combination with the Munsell Color Book, 1963 edition. Comparisons are made with the cultivar Marguerita. Where only a single value or description appears for the new cultivar, the same value or description applies to the cultivar Marguerita as well.

Botanical Classification: *Chrysanthemum morifolium*

| | Senorita | Marguerita |
|---|---|---|
| Bloom: | | |
| Size | 5½″ | 5¾″. |
| Fully expanded | 6″–6½″ | 6¼″–6¾″. |
| Borne | Singly on disbudded branches | |
| Stems | Strong | |
| Form | Daisy (duplex) | |
| Permanence | 12–14 days | |
| Color: | | |
| Center of flower | Yellow-green, 2.5GY6/8 | |
| Base of petals | Yellow-green, 2.5GY7/8 | |
| Inside of petals | Purple, 8.8P7/10 over lavender, 10P8.7/2 | Ivory, 10Y9/1. |
| Reverse of petals | Purple, 7.3P/7.3/7.9 over lavender, 10P8.7/2 | White, N9/. |
| Tonality from a distance | Lavender | Ivory white. |
| Petals: Discoloration | Lavender, 10P8.7/2 | Ivory, 10Y9/1. |
| Texture | Smooth on face with frequent seta on reverse side | Smooth. |
| Appearance and form | Open at base, broad multi-ridged keel, tapering to a blunt, slightly hooded tip; width of keel ⅝″. | Closed at base, flaring quickly to very broad multi-ridged keel, tapering to a blunt, slightly hooded tip; width of keel 1⅛″. |
| Arrangement | Composite, whorled on a single receptacle | |
| Persistence | Resist shatter | |
| Fragrance | Typical chrysanthemum | |
| Reproductive organs: | | |
| Stamen, anthers | 250+ | |
| Pollen | Abundant to none (functional sterility) | |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Spreading | |
| Height | Approximately 12″–15″ in a 4-cutting, 6″ pot grown as a disbudded pot, given 1–2 applications of B–9, the first approximately 1 week after pinching, and the second when necessary, approximately 3 weeks after planting; and 9 weeks tall treatment (1–2 weeks of long days) as defined in the timetables of Yoder Brothers, Inc., Barberton, Ohio, for the various recommended seasons. | Approximately 14″–17″ in a 4-cutting, 6″ pot grown as a disbudded pot, given 1–2 applications of B–9, the first approximately 1 week after pinching, and the second when necessary, approximately 3 weeks after planting; and 9 weeks tall treatment (1–2 weeks of long days) as defined in the timetables of Yoder Brothers, Inc., Barberton, Ohio, for the various recommended seasons. |
| Spread | Approximately 8″–10″ in a 4-cutting, 6″ pot grown as a disbudded pot, given 1–2 applications of B–9, the first approximately 1 week after pinching, and the second when necessary, approximately 3 weeks after planting; and 9 week tall treatment (1–2 weeks of long days) as defined in the timetables of Yoder Brothers, Inc., Barberton, Ohio, for the various recommended seasons. | Approximately 6″–8″ in a 4-cutting, 6″ pot grown as a disbudded pot, given 1–2 applications of B–9, the first approximately 1 week after pinching, and the second when necessary, approximately 3 weeks after planting; and 9 weeks tall treatment (1–2 weeks of long days) as defined in the timetables of Yoder Brothers, Inc., Barberton, Ohio, for the various recommended seasons. |

TABLE—Continued

| | Senorita | Marguerita |
|---|---|---|
| Foliage: | | |
| Top side | Dark yellow-green, 7.4GY2.3/4.0 | Very dark green, 8.9GY2.3/4.7. |
| Size | Length to width ratio 3:2 with length to 5¼" and width to 3½". | Length to width ratio 25:14 with length to 6¼" and width to 3½". |
| Quantity | Numerous | |
| Shape | Spatulate lobed | |
| Texture | Coarse | |
| Ribs and veins | Moderately prominent | |
| Edge | Moderately indented | |
| Serration | Moderate | |
| Under side | Medium green, 7.5GY5/4 | |
| Stipules | Prominent | |

We claim:

1. A new and distinct cultivar of chrysanthemum characterized particularly as to its uniqueness when compared with the cultivar Marguerita by its pink flower color and more fully petalled flowers which are approximately ¼" smaller in diameter; by its petals, which are aproximately ½" narrower, with numerous seta on the ventral side of the petal; less tolerance to temperatures lower than 60° F. for bud development, initiating and developing uniformly at such temperature, but having a response which is delayed; approximately 2 day earlier response at 60° F., except in early spring when the response is 2 days later; approximately 2" less vigor and approximately 2" more spreading habit; more responsive to growth regulation thereby making it easier to control height, and by its lighter green foliage, with smaller indentations on the leaf margin.

No references cited.

ROBERT E. BAGWILL, Primary Examiner